United States Patent
Thanoo et al.

(10) Patent No.: US 6,361,798 B1
(45) Date of Patent: Mar. 26, 2002

(54) METHOD AND APPARATUS FOR FORMULATING MICROSPHERES AND MICROCAPSULES

(75) Inventors: Bagavathikanun Chithambara Thanoo, Broadview Heights; James Murtagh, Hudson, both of OH (US)

(73) Assignee: Oakwood Laboratories, L.L.C., Oakwood, OH (US)

( * ) Notice: Subject to any disclaimer, the term of this patent is extended or adjusted under 35 U.S.C. 154(b) by 0 days.

(21) Appl. No.: 09/687,706

(22) Filed: Oct. 13, 2000

Related U.S. Application Data (62) Division of application No. 09/181,204, filed on Oct. 28, 1998, now Pat. No. 6,270,802.

(51) Int. Cl.[7] ............... A61K 9/50; A61K 9/14
(52) U.S. Cl. ................................... 424/489
(58) Field of Search ............... 424/489, 451; 264/4.1, 4.33, 4.6, 4.7; 428/402.21

(56) References Cited

U.S. PATENT DOCUMENTS

| | | |
|---|---|---|
| 3,645,911 A | 2/1972 | Van Beseauw et al. |
| 3,755,558 A | 8/1973 | Scribner |
| 3,773,919 A | 11/1973 | Boswell et al. |
| 3,891,570 A | 6/1975 | Fukushima et al. |
| 4,384,975 A | 5/1983 | Fong |
| 4,389,330 A | 6/1983 | Tice et al. |
| 4,652,443 A | 3/1987 | Yoshida et al. |
| 4,668,580 A | 5/1987 | Dahm et al. |
| 4,675,189 A | 6/1987 | Kent et al. |
| 4,692,188 A | 9/1987 | Ober et al. |
| 4,767,628 A | 8/1988 | Hutchinson |
| 4,818,542 A | 4/1989 | Deluca et al. |
| 4,898,696 A | 2/1990 | Sliwka |
| 4,954,298 A | 9/1990 | Yamamoto et al. |
| 5,049,322 A | 9/1991 | Devissaguaet et al. |
| 5,118,528 A | 6/1992 | Fessi et al. |
| 5,183,690 A | 2/1993 | Carr et al. |
| 5,304,377 A | 4/1994 | Yamada et al. |
| 5,330,767 A | 7/1994 | Yamamoto et al. |
| 5,389,379 A | 2/1995 | Dirix et al. |
| 5,407,609 A | 4/1995 | Tice et al. |
| 5,476,663 A | 12/1995 | Okada et al. |
| 5,480,868 A | 1/1996 | Kamei et al. |
| 5,534,269 A | 7/1996 | Igari et al. |
| 5,585,460 A | 12/1996 | Igari et al. |
| 5,611,971 A | 3/1997 | Maedera et al. |
| 5,631,020 A | 5/1997 | Okada et al. |
| 5,631,021 A | 5/1997 | Okada et al. |
| 5,718,921 A | 2/1998 | Mathiowitz et al. |
| 5,945,126 A | 8/1999 | Thanoo et al. ............... 424/489 |

FOREIGN PATENT DOCUMENTS

| | | |
|---|---|---|
| DE | 2237206 | 7/1971 |
| EP | 0274961 | 7/1988 |
| GB | 1405108 | 9/1975 |
| WO | WO95/13799 | 5/1995 |

OTHER PUBLICATIONS

Pharmaceutical Research 15(2) pp. 357–361.
24 Page Brochure, "Operating Guide", A/G Technologoes Corporation, Jan. 1996.
1 page Product Bulletin, "Steam–in–Place Hollow Fiber Ultrafiltration/Microfiltration Cartridges/Housings", date unknown.
1 page Product Bulletin, "Flexst and Benchtop Pilot Hollow Fiber System", date unknown.
24 Page Brochure, "Operating Guide", A/G Technologoes Corporation, Jan. 1997.

(List continued on next page.)

Primary Examiner—James M. Spear
(74) Attorney, Agent, or Firm—Watts Hoffmann Fisher & Heinke (57) ABSTRACT

A process and apparatus for making and formulating microcapsules and microspheres which can easily be maintained aseptic throughout all stages of the production process.

13 Claims, 2 Drawing Sheets

OTHER PUBLICATIONS 1 page Product Bulletin, "Avir Point–of–Use Air Filtration Systems", date unknown.

R. Jeyanthi et al., Effect of solvent removal technique . . . , Journal of Controlled Release 38 (1996) 235–244.

P.J. Burns et al., Evaluation of a new continuous process for preparation of progesterone . . . pp. 7603.

Sales Brochure, Ross intorduces new solid –liquid injection manifold (SLIM®) for instant addition of ingredients, Charles Ross and Son Compnay, Apr. 1995.

7 page article, "Investigation of an Optical Noncontact Gear Geometry Measurement System: Measurement of Pitch Errors and Tooth Profiles", Okuyama et al., Precision Engineering, vol. 16, No. 2, Apr. 1994.-

METHOD AND APPARATUS FOR FORMULATING MICROSPHERES AND MICROCAPSULES

This application is a Division of Ser. No. 09/181,204 filed Oct. 28, 1998 now U.S. Pat. No. 6,270,802.

BACKGROUND OF THE INVENTION

Microcapsules and Microspheres formed from various natural and synthetic polymers and resins have become popular delivery vehicles for various active agents such as drugs, diagnostic reagents and the like. Degradable microcapsules and microspheres are of particular interest for use in so called "depot" formulations, where delivery of the active agent over an extended period of time is desired. Despite the growing number of uses of microcapsules and microspheres, there remains a need for an economic, safe and reliable method for their manufacture and formulation that avoids the most significant wastes and expenses associated with existing methods, while simultaneously enabling the ability to aseptically formulate the products in a simple and efficient manner.

Processes for preparing microcapsules and microspheres typically involve the formation of at least one dispersed phase in a continuous phase. The dispersed phase typically includes the active agent. In the case of microspheres, the dispersed phase will also typically include polymer so that, upon solidification in the continuous phase, the dispersed phase becomes a microsphere. Microcapsules are similarly formed using multiple phases. In a typical practice, a water-oil-water (w/o/w) emulsion is formed, and the polymer caused to precipitate out of one phase onto the surface of a dispersed phase to form a capsule wall thereon upon solidification of the polymer. Once the capsules or spheres are produced, they must then be formulated into a finished dosage form.

Most microsphere processes result in a suspension of particles in a suspending liquid that is not the suspending liquid desired for the final dosage form. Current techniques for processing and formulating microspheres and microcapsules into the final dosage form typically involve dead end filtration and powder filling processes. Although the powder processes can be made aseptic, they tend to have the drawbacks of using large volumes of flammable solvents, capital intensive equipment trains are generally required for a fixed scale and they take a comparatively long time to produce a finished batch. Likewise, the time and capital expense associated with powder filling processes can put one at a significant competitive disadvantage.

There is a need for a process that can efficiently, economically and aseptically process and formulate microcapsules and microspheres into final dosage forms.

DISCLOSURE OF THE INVENTION

The present invention is directed to a method and apparatus for processing and formulating active agent containing polymer bodies, and more particularly microspheres and microcapsules. The method and apparatus according to the invention are ideal for formulating microcapsules and microspheres suitable for carrying drugs, diagnostic reagents, or various other active agents into final dosage form. The inventive method provides a simple, economic, efficient and aseptic means of formulating a product wherein the sterile field need not be compromised throughout the entire production cycle. As used herein, terms such as "sterile" and "aseptic" are taken to mean sterile or aseptic enough to meet current USP standards. The apparatus according to the invention is relatively inexpensive and easily broken down and sterilized, thereby significantly reducing capital expenditures associated with aseptic powder processes. Moreover, product batches can be produced with shorter cycle times than current processes for producing microcapsules and microspheres. A 500 gram bacth of leuprolide containing microspheres can be prepared and processed into final dosage vials on the order of three days.

The method and apparatus of the invention are most preferably employed to formulate microspheres produced in accordance with the process disclosed in co-pending application Ser. No. 08/800,924, filed Feb. 13, 1997 U.S. Pat. No. 5,945,126, incorporated herein by reference. Preferably, the active agent is a drug or diagnostic agent and the microspheres are intended for the delivery of such drug or diagnostic agent to a patient in need thereof. The preferred drugs may be peptide drugs, proteinaceous drugs, steroidal drugs, non-steroidal drugs, simple compounds and so on. A representative list of suitable drugs and other active agents may be found in U.S. Pat. Nos. 5,407,609, 4,767,628, 3,773,919 and 3,755,558, all incorporated herein by reference. Of particular interest are LH-RH agonists such as leuprolide, triptorelin, goserelin, nafarelin, historelin and buserelin, LH-RH antagonists, somatostatin and its analogs such as octreotide, human, salmon and eel calcitonin, growth hormones, growth hormone releasing hormones, growth hormone releasing peptide, parathyroid hormones and related peptides, interferon, erythropoietin, GM-CSF, G-CSF, thymosin, antitrypsin, enterostatin, and chemotherapy drugs, antibiotics and analgesics for regional administration. An especially preferred drug for use in the instant invention is leuprolide.

The advantages of the invention are accomplished by maintaining and processing the microspheres or microcapsules as a suspension. While significant advantages can be achieved by processing the product as a suspension, there is also a significant potential for product losses if adequate precautions are not taken to maintain the suspension and ensure proper product flow throughout the process.

Generally speaking, the formulating process of the invention involves the concentration, washing and. formulating of agent containing polymer bodies, i.e., microspheres or microcapsules, that are maintained in a suspension of a continuous phase. Typically, the continuous phase containing the polymer bodies is initially water, or water containing residual impurities from the process used to make the microspheres or microcapsules, such as surfactants, residual solvent and the like. In order to formulate the polymer bodies into a final product it is necessary to process the polymer bodies into an appropriate sterile concentration of polymer bodies in a suitable pharmaceutically acceptable diluent or carrier, i.e., formulating medium. The present process accomplishes this aseptically by processing the polymer bodies as a suspension using a filter capable of removing the continuous phase without deleteriously effecting the suspension of polymer bodies. The continuous phase which, as noted, can initially be water, but subsequently during the process can be other suspending media, including water for injection and formulating medium, is then cycled back to a process vessel as a suspension for further processing in subsequent phases. Advantageously, a hollow fiber filter provides an ideal means of accomplishing the concentration of the polymer bodies, and the replacement of the continuous phase with other continuous phases such as water and/or formulating medium.

In practicing the inventive method of formulating according to the invention, a suspension of agent containing polymer bodies in a continuous phase is provided in a process vessel. In a preferred embodiment the apparatus will employ only a single processing vessel, which serves to formulate the microspheres and microcapsules in accordance with the method described herein. However, configurations can be devised in which the process vessel performs multiple functions. For example, it can also serve as a solvent removal vessel as a preliminary step to the practice of the inventive method. Similarly, multiple process vessels can be employed in series, each functioning to perform one or more phases of the formulating process, such as a concentrating phase, a washing phase and a formulating phase, respectively.

Since one of the advantages of the invention is derived from the simplicity and limited capital costs of the apparatus used, it is generally preferred that a minimum number of vessels be employed. However, on larger scale processes, where significant volumes are to be processed, it may be necessary to employ two process vessels and hollow fiber filters in series to minimize losses. Thus, in another preferred embodiment, the first process vessel serves as a solvent removal vessel, into which a relatively large volume of formed or forming microspheres are directly transferred from a means for forming them, such as an in-line mixer, and also serves to perform a concentrating and washing phase. In order to minimize losses, a second process vessel and hollow fiber filter are employed to further reduce the volume and increase concentration, and also to perform the formulating phase.

While maintaining said polymer bodies in suspension in the process vessel, such as by magnetic stirrer, impeller, recirculation apparatus and the like, the continuous phase is replaced with a formulating medium by moving the suspension through the filter apparatus. Preferably, the suspension is circulated through the filter and back to the processing vessel, rather than to down stream vessels. Conceptually, any filter that is adapted to eliminate continuous phase and return the polymer bodies as a suspension to a process vessel will suffice for the practice of the invention, with the noted hollow fiber filter being preferred. As noted, the continuous phase will typically initially be water containing not only the polymer bodies, but also various impurities from the microsphere/microcapsule preparation process. Thus, while, depending upon the nature of the active agent and end use to which the product will be put it is possible to replace. the initial continuous phase directly with formulating medium, the process according to the invention will preferably include a washing phase. Likewise, since the concentration of polymer bodies in the initial continuous phase will generally be significantly less than the concentration required for the final product, the process will also preferably include a concentrating phase, in which the suspension is run through the filter to eliminate continuous phase. Once the suitable concentration of polymer bodies in the formulating medium is obtained, as ascertained by sampling and assaying the suspension from the processing vessel, the suspension of agent containing polymer bodies and formulating medium is removed from the process vessel for subsequent processing, such as filling into final product vessels.

The invention is also embodied in a novel and advantageous apparatus for formulating the agent containing polymer bodies. In particular, the apparatus employs a process vessel that is adapted to maintain a suspension of polymer bodies in a continuous phase that is coupled to the noted filter in a manner that enables the suspension to be processed through the filter so as to eliminate continuous phase, and thereafter return the suspension to the process vessel, or one or more additional process vessels, for further processing. To accomplish the further processing, the apparatus includes a source of formulating medium and, when a washing phase is employed, as source of wash water. The inventive apparatus thereby enables the microspheres or microcapsules to be processed as a suspension. Advantageously, the apparatus is relatively simple and inexpensive, and highly conducive to processing the polymer bodies aseptically.

As will be apparent, in its simplest configuration the apparatus will employ a single process vessel and filter combination that is coupled to a source of microspheres or microcapsules, as well as the water source and formulating medium source. However, it is likewise possible for a. plurality of filters and process vessels to be coupled in series, so that the output from a first processing vessel and filter can be transferred to a second process vessel and filter for, e.g., a washing step, which output may then be transferred to yet a third process vessel and filter for substitution of water from the washing step with formulating medium. Likewise, the separate vessels could all utilize the same filter. Other configurations will also be apparent to those of ordinary skill in the art in view of the instant disclosure.

As noted, many of the advantages of the present invention are derived from the ability of the apparatus to process the microspheres as a suspension. Thus, the preferred apparatus of the invention is configured using simple elastomeric tubing, peristaltic pumps and pinch clamps or similar devices. Such components not only advantageously add to the low costs associated with the invention, they enable the maintenance of the suspension by eliminating settling points and other areas where potentially significant losses can occur, such as mechanical valves, sharp turns, elbows and the like. The various components of the system are thus coupled in a manner that maximizes the ability of the system to maintain the polymer bodies in suspension. It is to be understood that the term "coupled" as used herein means that the various components are operatively coupled so that the contents of one element can move to another element, but can include intermediate elements and components.

In another aspect of the invention there is provided a method of making and formulating agent containing polymer bodies. The polymer bodies are formed by forming a dispersed phase comprising an active agent, and providing a continuous phase in which the dispersed phase will form an emulsion, at least one of the dispersed and continuous phases comprising polymer. The dispersed and continuous phases are introduced into a reactor vessel that includes means for forming an emulsion, and an emulsion of the dispersed phase in the continuous phase is formed causing the polymer to form microspheres or microcapsules containing the active agent. Likewise, a series of reactors may be used to form a double emulsion for forming microcapsules. Thereafter, the said emulsion is transported from the reactor vessel to a solvent removal vessel and solvent is removed therein. Once the desired level of solvent removal is obtained, the polymer bodies are formulated by maintaining them in suspension in accordance with the aforementioned formulating process. In a preferred embodiment, the means for forming an emulsion is an in-line mixer. In another aspect of the invention, the means for forming an emulsion is a static mixer.

Many additional features, advantages and a fuller understanding of the invention will be had from the following detailed description of the preferred embodiments and accompanying drawing.

DETAILED DESCRIPTION OF THE PREFERRED EMBODIMENTS

Figure 1:
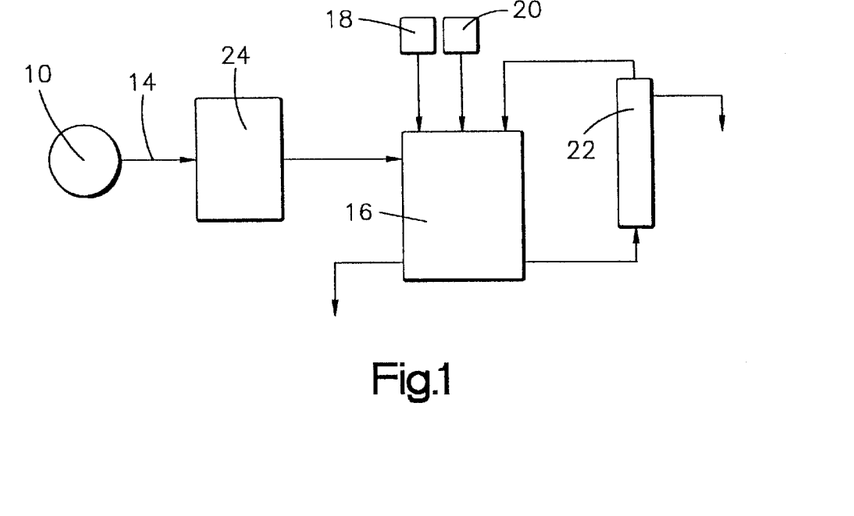
FIG. 1 is a stylized schematic flow diagram of the formulating process according to the invention.

Referring generally to FIG. 1, the formulating process of the invention can be described. Represented generally at 10 is a source of microspheres or microcapsules. As noted, the microspheres or microcapsules can be prepared by any means known in the art such as thermal processes, single and double emulsion processes and the like as set forth in, for example, U.S. Pat. Nos. 4,675,189, 5,534,269, 3,773,919, 5,611,971 and 4,767,628, incorporated herein by reference, static mixing processes as disclosed in Published International Patent Application No. WP 95/13799, incorporated herein by reference, by high intensity in-line continuous processing as set forth in co-pending application Ser. No. 08/800,924 now U.S. Pat. No. 5,945,126, incorporated herein by reference, and solution based processes such as disclosed in U.S. Pat. Nos. 5,407,609, 4,818,542 and 4,389,330, incorporated herein by reference. Preferably, source 10 is an in-line mixer for providing microspheres in accordance with the method disclosed in copending application Ser. No. 08/800,924 now U.S. Pat. No. 5,945,126.

The microspheres or microcapsules may be transferred from source 10 to a holding tank 24 via harvest line 14. Although in the preferred embodiment a suspension of solidified dispersed phase particles suspended in the continuous phase will generally be transferred to tank 24, depending upon the specific nature of the process for making the microspheres or microcapsules, the polymer bodies being transferred to the tank 24 may not yet be solidified or otherwise may still be in the process of forming. Transfer to the holding tank, in the case of the preferred in-line continuous process, can be accomplished by the pumping action of the in-line mixer itself, or otherwise by vacuum or pump action as would be apparent to those of ordinary skill in the art in view of the present disclosure. In another embodiment, the polymer bodies may be transfered to a process vessel that will serve as a solvent removal vessel as well as perform one or more of the concentrating, washing-and formulating steps.

Once an adequate volume of continuous phase containing the polymer bodies has been provided in holding tank 24, the formulating process according to the invention can commence. The particular volume introduced into tank 24 will vary depending upon the size of the particular apparatus employed and is essentially arbitrary as long as the material can act as a fluid and be maintained in. suspension as needed. Typically, the initial volume present in a solvent evaporation tank, or in holding tank 24 will be significantly greater than that being processed in formulating vessel 16, perhaps on the order of forty liters versus one to three liters. Likewise, the concentration of microspheres or microcapsules will be significantly more dilute than that required in the final formulation. Unlike open and dead end filtration systems, a significant advantage of the present invention is the ability to concentrate a large volume of dilute continuous phase into a small volume of concentrated continuous phase in a closed system in a fast, efficient and aseptic manner.

As seen in FIG. 1, formulating vessel 16 is coupled to a water for injection (WFI) source 18, a formulating medium source 20 and a hollow fiber filter 22. It is important in the practice of the preferred embodiment, where the advantages of a generally continuous process are to be obtained, to coordinate and control flow of material into and out of the formulating vessel 16. In this way suitable amounts of continuous phase containing agent containing polymer bodies, WFI and formulating medium can be selectively metered into formulation vessel 16 at appropriate rates and in appropriate amounts while keeping the volume in the formulating vessel 16 approximately constant.

Figure 2:
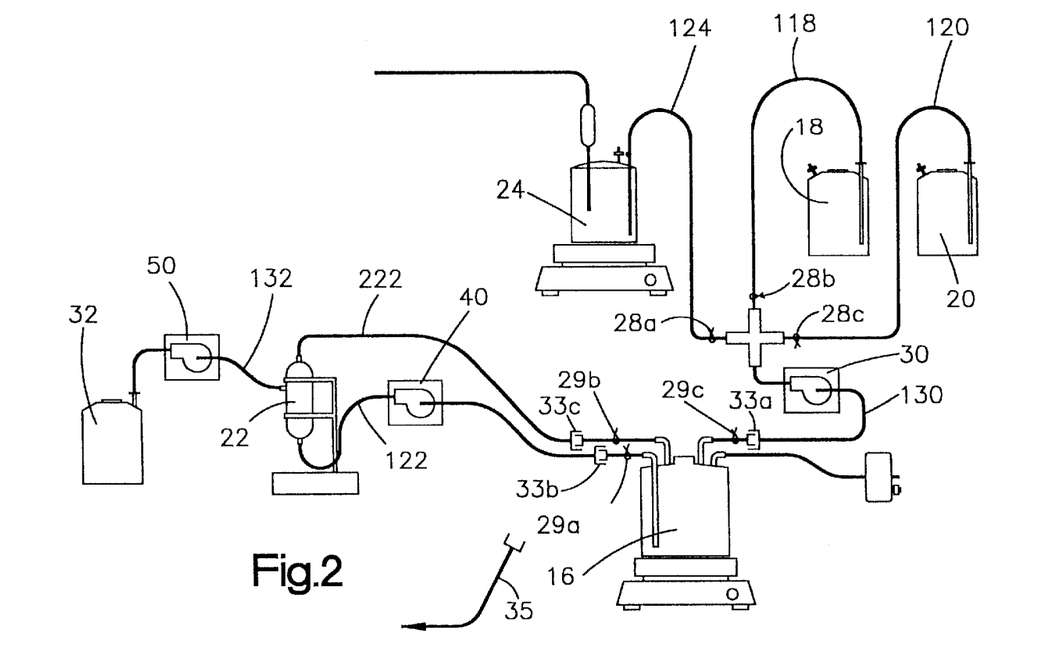
FIG. 2 is a stylized representation of an apparatus useful in carrying out the formulating process according to the invention.

As noted, because of the potential for significant losses it is important to maintain the polymer bodies in suspension. Settling of the polymer bodies leads to potentially significant losses, as well as clogging in the various lines and orifices. By maintaining the polymer bodies in a suspension, the advantageous method and apparatus of the invention are made possible. Thus, holding vessel 24 will include means for maintaining the polymer bodies in suspension, such as a magnetic stirrer in the case of smaller scale apparatus, or an impeller, recirculation apparatus or the like. Likewise, as seen in FIG. 2, holding tank 24, WFI source 18 and formulating medium source 20 are coupled to the formulation vessel 16 via elastomeric tubing lines 124, 118 and 120 respectively. Each line may be selectively closed from access to vessel 16 via suitable clamps, shown generally at 28. In this way, the use of valves or similar mechanisms for selectively controlling the flow of polymer body suspension to the formulation vessel that can potentially cause significant losses are avoided. The polymer body suspension, WFI and formulating medium are selectively pumped to formulating vessel 16 via peristaltic pump 30 and tubing line 130 which, again, helps to prevent losses. Other pumping apparatus suitable for use in the present invention may include rotary lobe pumps and centrifugal pumps. The principal consideration is the ability of the tubes, pumps and connections used in the present apparatus to facilitate the maintenance of the suspension and to eliminate or minimize losses through settling. Other means of maintaining the suspension and minimizing losses would be apparent to those of ordinary skill in the art in view of the instant disclosure.

As shown, formulating vessel 16 includes a plurality of ports for the introduction and removal of continuous phase containing polymer bodies to and from the vessel. Likewise, as will be apparent, the vessel 16 includes means for maintaining the polymer bodies in suspension therein (not shown). Suitable means may vary depending upon the scale of the apparatus, and will be apparent to those of ordinary skill in the art in view of this disclosure. Such means can include magnetic stirrers, impellers, recirculation devices and the like.

In the practice of the invention a suspension of polymer bodies, i.e., microspheres or microcapsules, in continuous phase is pumped into formulation vessel 16 via pump and tube 124. A suitable volume of suspension will vary depending upon the scale of the process. Volumes ranging from about 1 to 40 liters may be employed depending upon the scale of the apparatus. In the preferred process of formulating LH-RH agonist containing microspheres, a suitable starting volume for the apparatus employed is on the order of about 1 to 3 liters. Generally, the concentration of polymer bodies in the continuous phase that is introduced into the formulating vessel will not correspond to the concentration required for the final product. For example, the holding tank may contain on the order of 40 liters of continuous phase having a microsphere concentration on the order of about 2 to 3 grams per liter. Thus, while maintaining the polymer bodies in suspension in formulation vessel 16, the suspension undergoes a concentration phase.

During the concentration phase the suspension is pumped from the formulation vessel 16 via. peristaltic tubing 122 to hollow fiber filter 22. As the suspension passes through hollow fiber filter 22 continuous phase is removed by the filter, thereby concentrating the suspension of polymer bodies in the continuous phase. As shown, waste continuous phase, or permeate, removed by filter 22 is transferred to waste tank 32 via line 132 and pump 50. A pump is not required, but may be useful to control the rate of removal. After the suspension passes through the filter 22 it is transferred back to formulation vessel 16 via elastomeric tubing 222. The use of elastomeric tubing, such as silastic tubing, and peristaltic pumps advantageously enables the processing of the suspension according to the invention with a minimum of losses. With the apparatus currently employed, about 40 L of continuous phase from tank 24 is pumped into formulating vessel 16 at a rate of about 400 ml/min. This corresponds the rate at which the filter 22 removes continuous phase in the form of permeate. The continuous phase is continually pumped in and taken out at a rate of about 400 ml/min. until all of the continuous phase has been transferred from tank 24 and the volume in the formulating vessel 16 is on the order of 1–3 liters. In carrying out the process, the rate at which the continuous phase is pumped through the filter 22 via. tubing 122 and 222 is also important. With the preferred filter, the rate at which continuous phase is removed by the filter should not exceed about one third of the flow rate of continuous phase through the filter, otherwise flow and clogging problems can occur. Thus, with the preferred filter removing 400 ml/min the flow rate through the filter should be on the order of about 2 liters/min.

Figure 3:
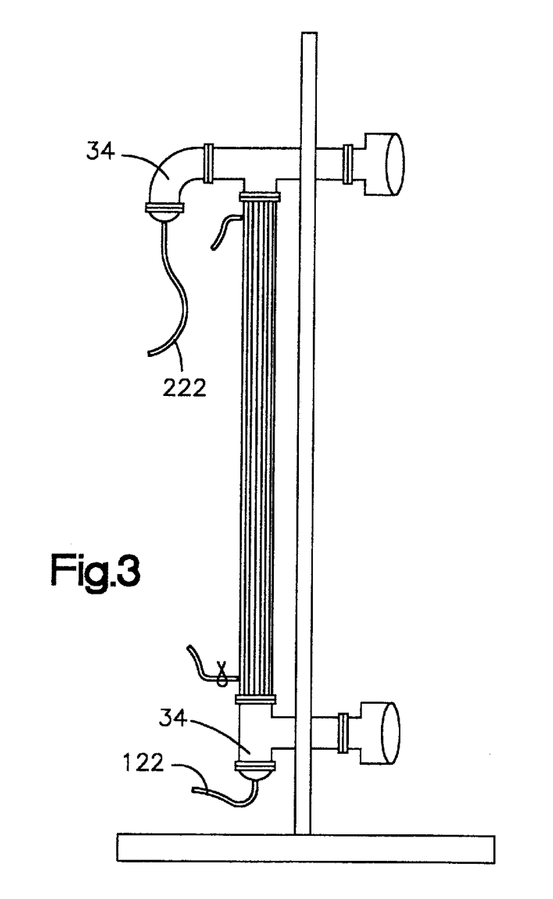
FIG. 3 is a stylized representation of a filter apparatus according to the invention.

The preferred configuration of hollow fiber filter 22 is seen best in FIG. 3. As shown, filter 22 is coupled via peristaltic tubing 122 and 222. In this way, no sharp turns or 90 degree elbows are present as a significant source of losses. The preferred filter 22 is the CFP-A-E-6A, 0.45 micron hollow fiber filter from A/G Technology, supported on a flexstand in the example. In the practice of the preferred embodiment the filter configuration has been modified to employ connections 34 in order to eliminate settling points, which would otherwise result in significant losses. For the scale of apparatus represented this filter serves to eliminate about 400 ml of continuous phase per minute. It employs a 1 mm diameter fiber, although fiber diameter and other filter parameters will vary depending upon particle size, the nature of the formulating medium and the like. Selection of suitable filter units will be apparent to those of ordinary skill in the art in view of the instant disclosure. For a typical pharmaceutical product, polymer body concentrations on the order of 40 to 200 grams per liter will be required. In the case of the preferred LH-RH agonist containing microspheres, a target concentration of from about 27 mg/ml to about 150 mg/ml is desired depending upon the final dosage form. In practice, it is desirable to aim for a suspension that is slightly more concentrated than required for the final product because a dilution correction to final dosage concentration is typically a simpler procedure than a concentrating correction. Given the volume of permeate generated by the particular filter and pump used, and the flow rate of continuous phase through the filter, one can readily approximate the time necessary to obtain the desired concentration or, in the case of the washing and formulating phases, the approximate time necessary to replace one continuous phase with another. Verification is then readily ascertained by monitoring the weight of permeate.

Once the suspension of polymer bodies in the formulation vessel has been concentrated to the approximate concentration of microspheres or microcapsules necessary in the final product, clamp 28b on tubing 118 is removed to allow water for injection to be introduced into vessel 16 from WFI source 18 to commence a washing phase. In the washing phase the polymer bodies are maintained in suspension in vessel 16 and the suspension pumped to filter 22 via tubing 122. In the preferred embodiment, the volume in the formulating vessel 16 is maintained at about 1–2 liters by coordinating the pumps 30 and 50 so that the flow rates of water in from source 18 and continuous phase permeate out through line 132 are matched at 400 ml/min. As noted, with the filter removing approximately 400 ml/min., and the flow rate in loop 122/22/222 maintained at about 2 l/min., the time required to replace the volume of continuous phase with an equal volume of water for injection can be readily determined. In the preferred embodiment, additional passes are made to ensure a complete washing.

Once the washing phase is complete the formulating phase is commenced. The WFI source 18 is closed and the formulating source 20 opened by selectively clamping and unclamping the appropriate clamps 28b and 28c. Formulating medium is thus pumped into formulating vessel 16 via pump and tubing 120 and 130. As with the washing phase, the pumps 30 and 50 are coordinated to maintain the volume in the formulating vessel and the process of passing the suspension of polymer bodies through filter 22 commences. The polymer bodies are maintained in suspension in vessel 16 and the suspension pumped to filter 22 via tubing 122 until the WFI is replaced with formulating medium. To ensure complete formulation, the preferred embodiment passes the suspension through filter 22 in excess of the theoretical time necessary to replace the volume in the vessel 16.

Once formulated, the composition may be assayed for determination of drug content of the suspension to determine the final required dosage. As would be apparent to those of ordinary skill in the art in view of this disclosure, final dosage adjustment is determined by sampling and assaying the suspension and performing a concentrating or diluting correction as needed.

Once the desired concentration of polymer bodies in the formulating medium is obtained, the volume of formulated composition from vessel 16 may be removed and transferred for subsequent processing into final product. In the preferred process the formulated composition is transferred from vessel 16 to an aseptic filling machine where the product is filled into product vials or other suitable containers. This is done aseptically by disconnecting tubing 122 and connecting transfer tubing 35 which couples to 29a of vessel 16 to the filling station, all the while maintaining the composition sterile and in suspension.

It will be apparent that irrespective of the particular method of making the microspheres or microcapsules, solvent removal is generally important, especially when the resulting microspheres are intended for clinical applications. However, in some instances it may be possible to bypass the solvent evaporation tank and transfer the microspheres or microcapsules directly to the formulating vessel 16. Likewise, it may also be desirable for formulating vessel 16 to serve both as the formulating vessel and as the solvent evaporation tank.

The process according to the invention will now be exemplified by the following non-limiting example and with reference to the accompanying drawings.

EXAMPLE

Initially, a suspension of microspheres of leuprolide acetate prepared by the process according to the aforementioned co-pending application Ser. No. 08/800,924 U.S. Pat. No. 5,945,126 is transferred through a wet sieve into the holding tank from a solvent evaporation tank (not shown). When all of the suspension, in this example approximately 40 liters, is transferred to the holding tank 24, the pump is stopped and the formulating process begins. The concentration phase is commenced by moving the suspension through the hollow fiber filter, A/G Technologies CFP-A-E-6A, 0.45 micron, supported on a Flexstand.

Approximately 1.2 L of suspension is moved into the process vessel using peristaltic pump 30 and the suspension maintained in the process vessel by magnetic stirrer. Peristaltic pump 40 is started to circulate the suspension through the hollow fiber filter at a rate of about 1.75 L/min. Peristaltic pump 50 on the filter outlet is adjusted to obtain a permeate flow from the filter to the waste tank of about 400 ml/min. The flow rate of peristaltic pumps 30 and 50 are matched to maintain from about 1000 ml to 1300 ml of the suspension in the formulating vessel. The circulation of the suspension through the hollow fiber filter unit is maintained by peristaltic pump 40 and continued until approximately all 40 liters of the suspension is transferred from the holding tank 24 to the formulating vessel 16. The permeate flow from the filter is reduced to approximately 300 ml/min to achieve more circulation of the retained suspension (retentate) through the filter and prevent the microspheres from settling in the circulation path. This also helps reduce microsphere or microcapsule adherence to the wall of the filter. After approximately 90 minutes, the concentration phase was complete. The volume in vessel 16 at the end of the concentration phase was 1.10 L, and the weight of permeate was 36.25 Kg.

To commence the washing phase clamp 28a is closed and clamp 28b opened to permit water from the WFI vessel to enter the formulating vessel 16 via pump 30. Approximately 1.2 L of suspension is maintained in the formulating vessel by adjusting peristaltic pump 30. The suspension of WFI and polymer bodies is circulated through the hollow fiber filter until approximately 10 kg of WFI is mixed with the suspension. This is determined by measuring the weight of the permeate waste vessel. In this example, washing was complete after about 20 minutes and the weight of permeate was 9.96 kg.

The formulating phase is commenced to exchange the formulating diluent or medium for the WFI. Clamp 28b is closed and clamp 28c opened. The circulation rate through the hollow fiber filter is maintained at approximately 2 L/min. and the permeate flow rate is maintained at approximately 300 ml/min. Circulation of the formulating medium and polymer bodies through the filter is continued until about 10 L (i.e., 10 kg) of the formulating medium has been processed. As with the previous step, this may be determined by monitoring the weight of the permeate waste tank. In this example, the starting weight of the permeate waste was 10 kg and the final weight 20.06 kg, with the formulating step thus being completed after about 30 minutes.

To ensure final product specifications, it is to necessary to sample and fine tune the polymer body concentration depending upon the final desired dosage, which in turn depends upon the particular drug and polymer body morphology employed. This is accomplished by determining the volume of the suspension in the formulating vessel and reducing it to 700 ml. Once this volume is obtained, pump 50 is stopped. The direction of pump flow on pump 40 is then quickly changed to draw the suspension from the hollow fiber filter into the formulating vessel. When air bubbles start coming through the dip tube of the formulating vessel the pump is stopped and clamps 29a, b and c are closed. Quick connects 33a, b and c are disconnected and the junctions wrapped with sterile foil. While the mixing rate is maintained in formulating vessel the suspension is sampled.

Four 4×5 cc sample vials were labeled A, B, C and D. Using an 18 gauge 9" needle with stopcock through the septum on the vessel 16 approximately 2 ml of the suspension was drawn into a syringe. The syringe was disconnected from the needle and the 2 ml transferred into vial A. This procedure was repeated with the remaining vials while insuring that the needle remained in the septum of the suspension vessel. The vials were tare weighed. The suspension in vials A, B, C and D weighed 2.17 g, 2.01 g, 2.19 g, and 2.75 g, respectively. The samples were then tested for drug content and the suspension in the process vessel maintained by mixing until the results obtained. Once the results are obtained, stirring was stopped and the formulating vessel was quickly moved to a balance and the weight of the suspension therein determined to be 1173 g. For this drug if assay value is less than 7.5 mg/g, then a concentrating adjustment must be made. If the assay value is greater than 7.5 mg/g, then a diluting correction must be made. The assay in this example indicated that the drug content of leuprolide acetate was 9.6 mg/g, thereby requiring a dilution correction. By multiplying by the weight of the suspension and calculating the weight of suspension necessary to obtain 7.5 mg/g of leuprolide acetate it was determined that an additional 328 g formulating medium needed to be added.

The adjustment is easily made by reconnecting the quick connect 33a, opening clamp 28c and introducing the additional amount of formulating medium.

EXAMPLE 2

Figure 4:
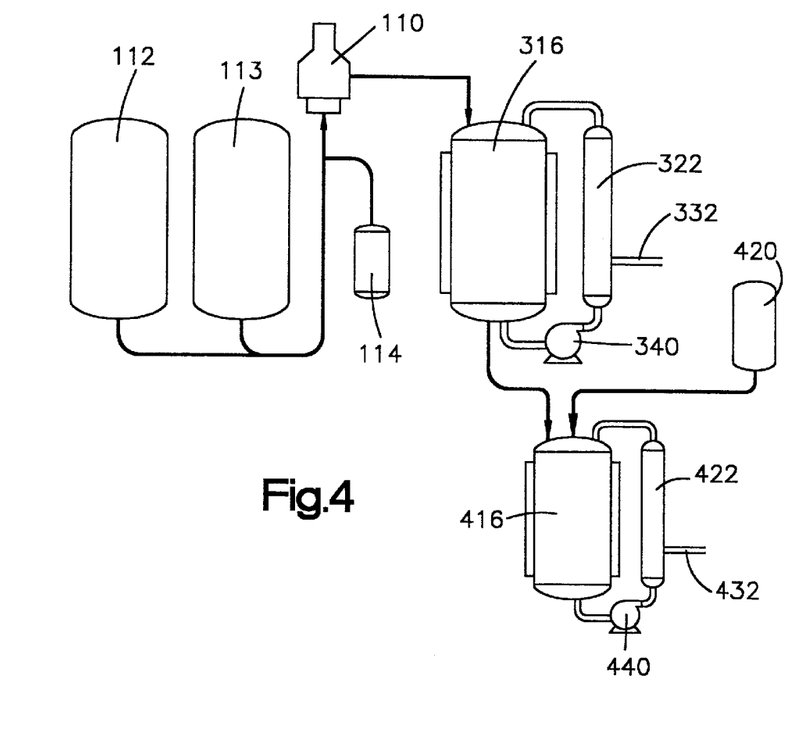
FIG. 4 is a stylized representation of another apparatus according to the invention.

With reference to FIG. 4, a suspension of microspheres containing an active drug substance can be processed in the identical way as the following example performed on blank, polymer only, microspheres. Microspheres were prepared by the process according to the aforementioned co-pending application Ser. No. 08/800,924 U.S. Pat. No. 5,945,126. Aqueous continuous phase, containing 0.35% PVA, from continuous phase tank 112, and dispersed phase comprised of a solution of 14.7 % PLGA polymer 503H from Boeringer Ingelheim, 66.2% methylene chloride and 19.1% methanol, from dispersed phase tank 114 was metered into a Silverson in-line mixer at a ratio of 80:1 and a rate of 2 liters per minute. The impeller in the mixer was run at a rate of 7000 rpm to cause the formed or forming microspheres to exit the mixer and enter vessel 316 (Model PTT-75-20-B 20 gallon jacketed 316 L stainless steel pressure vessel, Walker Stainless Steel Co) at a rate of 2 liters per minute. In this example, vessel 316 serves as both a solvent removal vessel and a processing vessel for the concentrating and washing steps.

In the previous example, the amount of microsphere suspension that, could be processed was limited to 40 liters due to the size of the holding tank 24 (FIG. 2). In this case, the bottom drain of the vessel 316 is connected to a Watson-Marlow large volume peristaltic pump 340 by sanitary connections (Tri-clover) using silastic tubing (½"ID)). The outlet of the peristaltic pump is connected to the bottom fitting of a hollow fiber filter 322 (A/G Technologies Model CFP4-E-55A, 0.45μ). The microsphere suspension flows through the hollow fiber filter and is returned to the vessel 316. After the vessel 316 has filled with 40 L of microsphere suspension, the peristaltic pump 340 is started at a flow rate of 15 liters per minute through the hollow fiber filter 322. The permeate flow out of line 332 is adjusted to 2 liters per minute, and the system is now running at a steady state such that newly formed microspheres are entering the vessel 316 at 2 liters per minute, the 40 liters of suspension are recirculating through the hollow fiber filter at 15 liters per minute, and 2 liters per minute of microsphere free permeate are being delivered to a waste container via line 332. In this example, the system was utilized to harvest and formulate microspheres delivered to the system at 2 liters per minute for a total time of one hour and fifty-two minutes. The concentration of the microsphere suspension is about 2.5 g of microspheres per liter, and the total amount of microspheres formed was 500 g. Thus at the end of the above concentration step, 500 g of microspheres were concentrated from an initial concentration of about 2.5 g per liter to a final concentration of 12.5 g per liter.

Removal of excess solvent from the microspheres was accomplished in the same equipment by continuing above process while adding wash solvent (in this case water) from wash water source 113 to the system at a rate of 2 liters per minute using a peristaltic pump (not shown) and continuing to draw off hollow fiber filter permeate at 2 liters per minute. Thus the volume and concentration of the microsphere suspension remained constant while the solvent concentration of the suspending fluid was reduced from an initial value of 6,360 ppm methylene chloride (determined by headspace gas chromatography) to a value of 2,618 ppm in twenty minutes.

Residual solvent in the microspheres is not readily removed by processing at room temperature. While the solvent in the suspending medium was reduced by two thirds during the above washing step, the residual solvent level in the microspheres themselves was reduced from about 80,000 ppm to about 50,000 ppm. Raising the temperature of the system is needed in order to reduce the residual solvent level of the microspheres to acceptably low levels. This is accomplished by continuing to deliver wash solvent (now water at 40° C.) at 2 liters per minute and raising the jacket temperature of the holding tank to 40° C. This was accomplished in 30 minutes, and the residual solvent in the suspending medium was found to be 1,092 ppm. The residual solvent in the microspheres was 18,000 ppm. This process can be continued until the residual solvent in the microspheres is reduced to acceptable levels. For the blank microspheres in this example, the residual solvent level in the microspheres was found to be about 13,000 ppm in 30 minutes of processing at 40° C.; 8,000 ppm in 50 minutes, 5,000 in 85 minutes, and finally 4,600 ppm in 100 minutes. The process can be continued to achieve still lower levels of residual solvents. In previous trials of leuprolide acetate, microspheres processed by this technique using smaller sized equipment (total amount of microspheres 10 g) , residual solvent levels of less than 71 ppm were achieved. In yet another run of blank microspheres using the smaller equipment, residual solvent levels of less than 500 ppm methylene chloride were achieved.

The washed, solvent reduced microspheres in ambient temperature water were reduced further in volume by transferring them to a smaller vessel 416 and continuing to pump (Watson Marlow 603S) the suspension through at 5 liters per minute through a second hollow fiber filter 422 (A/G Technologies, model CFP-4-E-9A,0.45 $\mu$), via pump 440, and drawing off water at 1 liter per minute, until the total 500 g of microspheres was suspended in 5 liters of water. The transfer to a second, small vessel was needed only to minimize the amount of microspheres lost in tubing and the like. Since the internal volume of the large pump, tubing and hollow fiber filter is nearly 2 liters, when the volume is reduced to 5 liters the 2 liter potential hold up in the pump and filter cycle of the first tank and filter is nearly 40% of the total volume. Thus, to minimize potential losses in the cycle, the suspension is transferred to the smaller vessel cycle at 416. After the microsphere suspension was brought down to a volume of 5 liters, the final formulating medium was delivered into the system at 1 liter a minute while fluid was removed through the hollow fiber at 1 liter per minute. This was continued for 50 minutes, until the microspheres were ready to aseptically fill into vials and freeze dried.

Many modifications and variations of the invention will be apparent to those skilled in the art in light of the forgoing detailed disclosure. Therefore, within the scope of the appended claims, the invention can be practiced otherwise than as specifically shown and described.

What is claimed is:

1. An apparatus for formulating agent containing polymer bodies comprising a process vessel adapted to maintain a suspension of agent containing polymer bodies in a continuous phase, said process vessel coupled to a formulating medium source and adapted to selectively receive formulating medium from said formulating medium source, said apparatus further comprising a filter adapted to receive said suspension and remove continuous phase while maintaining said polymer bodies in suspension and coupled to said process vessel in a manner effective to return said polymer bodies to a process vessel while maintaining said polymer bodies in suspension.

2. The apparatus of claim 1 wherein said filter is a hollow fiber filter.

3. The apparatus of claim 1 wherein said apparatus is configured so that said filter returns said polymer bodies to the same process vessel.

4. An apparatus for formulating agent containing polymer bodies comprising a process vessel adapted to maintain a suspension of agent containing polymer bodies, said process vessel coupled to a water source and to a formulating medium source and adapted to selectively receive water and formulating medium from said respective water and formulating medium sources, said apparatus further comprising a filter adapted to receive said suspension and remove continuous phase while maintaining said polymer bodies in suspension and coupled to said process vessel in a manner effective to return said polymer bodies to a process vessel while maintaining said polymer bodies in suspension.

5. The apparatus of claim 4 wherein said apparatus is configured so that said filter returns said polymer bodies to the same process vessel.

6. An apparatus for making and formulating agent containing polymer bodies comprising means adapted to form an emulsion of an agent containing dispersed phase in a continuous phase and effective to produce agent containing polymer bodies suspended in said continuous phase, said means coupled to a process vessel adapted to maintain a suspension of said agent containing polymer bodies, and a filter adapted to receive said suspension from said process vessel and remove continuous phase while maintaining said polymer bodies in suspension.

7. The apparatus of claim 6 wherein said filter is a hollow tube filter.

8. The apparatus of claim 6 further including a solvent removal vessel interposed between said means for forming an emulsion and said process vessel.

9. The apparatus of claim 6 wherein said filter is coupled to said process vessel in a manner effective to maintain said polymer bodies in suspension so that losses are no greater than about 10%.

10. The apparatus of claim 6 further including a water source and a formulating medium source coupled to said process vessel in a manner effective to enable the selective introduction of water and formulating medium to said process vessel.

11. The apparatus of claim 6 wherein said filter is coupled to said process vessel in a manner effective to circulate said suspension of polymer bodies from said process vessel and back to said process vessel.

12. The apparatus of claim 6 wherein said means adapted to form an emulsion is an in-line mixer.

13. The apparatus of claim 6 wherein said means adapted to form an emulsion is a static mixer.

* * * * *